United States Patent
Stephens et al.

(10) Patent No.: US 7,378,083 B2
(45) Date of Patent: May 27, 2008

(54) STABLE COSMETIC COMPOSITION COMPRISING A SELF-TANNING AGENT

(75) Inventors: Alison Fiona Stephens, Cookham (GB); Teresa Barbara Crook, Camberley (GB)

(73) Assignee: The Procter & Gamble Company, Cincinnati, OH (US)

( * ) Notice: Subject to any disclaimer, the term of this patent is extended or adjusted under 35 U.S.C. 154(b) by 803 days.

(21) Appl. No.: 10/842,585

(22) Filed: May 10, 2004

(65) Prior Publication Data

US 2004/0241113 A1 Dec. 2, 2004

(51) Int. Cl.
*A61Q 17/04* (2006.01)
*A61Q 17/00* (2006.01)
*A61Q 19/04* (2006.01)
*A61Q 19/00* (2006.01)
*A61K 8/02* (2006.01)

(52) U.S. Cl. .......................... 424/59; 424/60; 424/400; 424/401

(58) Field of Classification Search .................. 424/59, 424/60, 400, 401; 564/355; 568/413, 414
See application file for complete search history.

(56) References Cited

U.S. PATENT DOCUMENTS

| 6,197,287 | B1 | 3/2001 | Mallo et al. |
| 6,231,837 | B1 | 5/2001 | Stroud et al. |
| 2001/0051686 | A1 | 12/2001 | Tabacchi et al. |

FOREIGN PATENT DOCUMENTS

| WO | WO 88/01164 | 2/1988 |
| WO | WO 98/00098 A1 | 1/1998 |

OTHER PUBLICATIONS

T.Kurz (P043, "The Color of DHA Tan", poster, International Federation of Societies of Cosmetic Chemists (IFSCC) conference in Venezia (1994).
"Simulgel™ NS—An emulsifying/thickeningpolymer . . . for New Sensations" Documentation by the manufacturer SEPPIC, from Paris, France. Published on Jul. 2, 2001. XP002260687 p. 19, paragraph 5 p. 34.

*Primary Examiner*—Shelley A. Dodson
(74) *Attorney, Agent, or Firm*—Bridget Murray; Cynthia Clay; Eileen L. Hughett

(57) ABSTRACT

Stable topical compositions having a pH of from 3.5 to 4.5 comprising a self-tanning agent, a polymer and a polyhydric alcohol humectant. The compositions of the present invention are highly stable, and deliver high levels of active self-tanning agent to the skin upon topical application.

27 Claims, No Drawings

US 7,378,083 B2

STABLE COSMETIC COMPOSITION COMPRISING A SELF-TANNING AGENT

TECHNICAL FIELD OF THE INVENTION

The present invention is directed towards cosmetic compositions comprising a self-tanning agent having good shelf stability, good application characteristics and imparting excellent skin colouration without unacceptable orange discolouration.

BACKGROUND OF THE INVENTION

A wide variety of cosmetic compositions containing self-tanning agents have been used to increase the pigmentation of the skin. These compositions have been used to create artificial tans, bronzing the skin in a similar fashion to exposure to the sun. These compositions are typically quite unstable, having poor shelf life. This is thought to be due to the highly reactive nature of the self-tanning agents therein.

The prior art teaches several solutions to the problem of stability of self-tanning agents in cosmetic compositions. U.S. Pat. No. 6,231,837 B1 teaches the use of polyethoxyglycols such as ethoxydiglycol and polyols to stabilise self-tanning agent-containing compositions. WO 98/00098 teaches the combination of self-tanning agents and cross-linked non-emulsifying siloxane elastomers to form stable emulsions. U.S. Pat. No. 6,197,287 discloses anionic polymers and compositions comprising them, including self-tanning agents. However, these solutions are not entirely satisfactory at maintaining the stability of self-tanning agent-containing formulations or have other disadvantages such as poor skin feel when topically applied.

It is desirable to provide stable cosmetic compositions comprising a self-tanning agent to provide a unique level of skin tanning that lifts the skin tone. Furthermore, it is desirable to provide a cosmetic composition comprising both self-tanning skin colouring agents and chronic skin care actives that act synergistically to maximise skin tone enhancement. It is further desirable to include chronic skin regulating agents in the compositions of the present invention to improve the skin barrier and so minimise any areas of dry or compromised skin. This is desirable as dry skin areas have uneven uptake of colour resulting in a blotchy or patchy result.

A supplier brochure by SEPPIC (XP-002260687), entitled "Simulgel™ NS—An emulsifying/thickening polymer . . . for New Sensations" disclose a self-tan gel-cream composition comprising 5% by weight Simulgel NS and 2.00% by weight dehydroxyacetone, but no humectant.

A summary of a poster by T. Kurz (P043, "The Color of DHA Tan") presented at an International Federation of Societies of Cosmetic Chemists (IFSCC) conference in Venezia (1994) relates to the possibilities to influence the hue of a DHA tan. The influence of having a moisturizer is discussed, and according to this document, "addition of 10% moisturizer does not increase the intensity of the tanning, it even seems to lead to a slight reduction of it". Different results were obtained at a level of 20% moisturizer.

SUMMARY OF THE INVENTION

The present invention is directed to cosmetic compositions comprising:
a) a self-tanning agent conforming to the general formula;

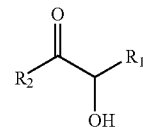

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$; and
b) a cross-linked anionic polyelectrolyte polymer, said polyelectrolyte polymer comprising;
  i) from 58.7% to 89.9999% by weight of the polyelectrolyte polymer of a monomer comprising a strongly acidic function;
  ii) from 9.9999% to 40% by weight of the polyelectrolyte polymer of at least one neutral monomer comprising a hydroxy alkyl acrylate; and
  iii) from 0.0002% to 1.3% by weight of the polyelectrolyte polymer of a diethylenic or polyethylenic cross-linking agent;
c) a polyhydric alcohol humectant;
said composition further having a pH of from 3.5 to 4.5.

The invention preferably comprises from 5 to 30% by weight of the polyhydric alcohol humectant, more preferably from 5 to 15%.

The present invention is further directed towards providing skin care kits, methods of regulating skin condition and methods of manufacture of the cosmetic composition.

The compositions of the invention are stable, useful for topical application and for providing essentially immediate (i.e. acute) improvement in skin appearance following topical application. Without being limited by theory, it is believed that this acute improvement results at least in part from an immediate increase in skin tone by the self-tanning skin colouring agent. The compositions of the present invention have very good acute benefits on application, namely producing good skin tone without the skin appearing unnatural or orange in effect.

These and other features, aspects, and advantages of the present invention will become evident to those skilled in the art from a reading of the present disclosure.

DETAILED DESCRIPTION OF THE INVENTION

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

The cosmetic compositions of the present invention comprise a self-tanning agent. As used herein, the term "self-tanning agent" includes α-hydroxy aldehydes and ketones such as dihydroxyacetone and structurally related compounds. This definition includes all such agents that are similarly useful in producing or inducing the artificial tanning process in human skin. Accordingly, the compositions of the present invention comprise an α-hydroxy aldehyde or ketone of the formula (I):

wherein $R_1$ is H, $CH_2OH$, $CHOHCH_2OH$, $CH(OH)CH$ (=O), $CH(OCH_3)CH$(=O), $CH(NH_2)CH$(=O), or $CH(NH\text{-Phenyl})CH$(=O); and $R_2$ is H or $CH_2OH$. Dihydroxyacetone (DHA) itself may be represented by the following general structural formula:

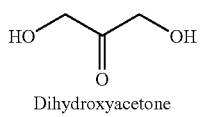

Dihydroxyacetone

A number of other compounds are already known in the art as capable of producing or inducing the same artificial tanning process in human skin as is produced or induced by DHA. Some of these are structurally similar to DHA, and include the following:

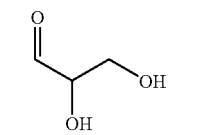
Glyceraldehyde

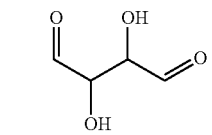
2,3-dihydroxy-succindialdehyde

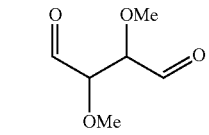
2,3-Dimethoxysuccindialdehyde

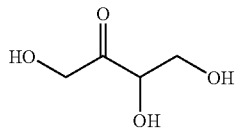
Erythrulose

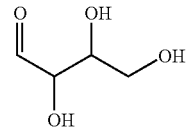
Erythrose

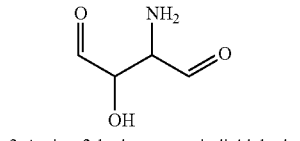
2-Amino-3-hydroxy-succindialdehyde

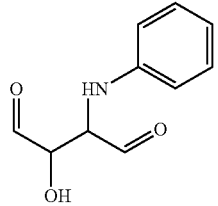
2-Benzylamino-3-hydroxy-succindialdehyde

Preferably, the self-tanning agent comprises DHA, erythrulose, or mixtures thereof, more preferably DHA. Preferably the compositions of the present invention comprise from 0.1% to 10% of the self-tanning agent. More preferable, the compositions of the present invention comprise from 1.0% to 3.5%, more preferably still from 1.2% to 2.5% of the self tanning agent.

The cosmetic compositions of the present invention also comprise a branched and/or cross-linked anionic polyelectrolyte polymer. As used herein, "branched and/or cross-linked anionic polyelectrolyte polymer" includes non-linear polymers in the form of a three-dimensional network that is insoluble in water but swellable in water and thus leading to the production of a chemical gel. The composition according to the invention can comprise cross-linked units and/or branched units. The branched and/or cross-linked anionic polyelectrolyte polymer comprises at least one monomer possessing a strongly acidic function, co-polymerized with at least one hydroxy alkyl acrylate neutral monomer.

Preferably, the compositions of the present invention comprise a branched and/or cross-linked anionic polyelectrolyte polymer that is the result of the copolymerization of its precursor monomers that is carried out at pH 4.0 or below. Preferably the anionic polyelectrolyte comprises from 30% to 89.9999% by weight of the polyelectrolyte polymer of a monomer having a strongly acidic function. As used herein, the term "monomer having a strongly acidic function" includes monomers having a pKa of less than 3. The pKa is measured by titration of the monomer having a strongly acidic function with a strong base in aqueous solution according to methods well known in the art. The strongly acidic function of the monomer containing it is preferably a sulphonic acid function or a phosphonic acid function, partially or totally salified. Non-limiting examples of monomers having a strongly acidic function group suitable for use herein include partially or totally salified 2-methyl-2-[(1-oxo-2-propenyl)amino]-1-propanesulphonic acid, partially or totally salified styrenesulfonic acid, or mixtures thereof. Preferably, the monomer comprises the partially or totally salified alkali metal salt or an ammonium salt of 2-methyl-2-[(1-oxo-2-propenyl)amino]-1-propanesulphonic acid.

Non-limiting examples of the at least one hydroxy alkyl acrylate neutral monomer suitable for use herein include 2-hydroxy-ethyl acrylate, 2,3-dihydroxypropyl acrylate, 2-hydroxy-ethyl methacrylate and 2,3-dihydroxypropyl methacrylate, or an ethoxylated derivative, with a molecular weight from 400 to 1000 of each of these esters, or mixtures thereof, preferably 2-hydroxy-ethyl acrylate. Polyelectrolyte polymers useful herein preferably comprise from 9.9999% to 40% by weight of the polyelectrolyte polymer of the at least one hydroxy alkyl acrylate neutral monomer.

More preferably, the compositions of the present invention comprise a reverse latex polymer comprising a branched and/or cross-linked anionic polyelectrolyte polymer, said polymer comprising partially or totally salified 2-methyl-2-[(1-oxo-2-propenyl)amino]-1-propanesulfonic acid, copolymerized with 2-hydroxyethyl acrylate. More preferably still, the polymer comprises 30% to 89.9999%, preferably 50% to 89.9999%, of the monomer units of partially or totally salified 2-methyl-2-[(1-oxo-2-propenyl) amino]-1-propanesulfonic acid (MPSA) by weight of the polyelectrolyte polymer. Even more preferably, the cross-linked anionic polyelectrolyte polymer comprises, from 58.7% to 89.9999% of sodium salt or of ammonium salt of 2-methyl-2[(1-oxo-2-propenyl)amino]-1-propanesulfonic acid by weight of the polyelectrolyte polymer and from 9.9999% to 40% of 2-hydroxyethyl acrylate by weight of the polyelectrolyte polymer.

The polymers for use in the present invention preferably comprise an anionic polyelectrolyte that is crosslinked and/ or branched with a diethylenic or polyethylenic compound at levels of from 0.0002% to 1.3%, preferably from 0.001% to 0.8%, more preferably from 0.01% to 0.6% by weight of the polyelectrolyte polymer. Non-limiting examples of crosslinking agents and/or branching agents suitable for use herein include ethylene glycol dimethacrylate, sodium diallyloxyacetate, ethylene glycol diacrylate, diallylurea, trimethylolpropane triacrylate, methylene bisacrylamide, or mixtures thereof, preferably methylene bisacrylamide.

Preferably, the cosmetic compositions of the present invention comprise from 0.1% to 2.0% of the branched and/or cross-linked anionic polyelectrolyte polymer, more preferably from 0.2% to 1.2%, more preferably still from 0.4% to 0.8%.

Non-limiting examples of commercially available branched and/or cross-linked anionic polyelectrolyte polymer compositions suitable for use herein include Simulgel NS™, available from Societe D'Exploitation de Produits Pour Les Industries Chimiques (SEPPIC), Paris, France.

The compositions of the invention comprise at least one polyhydric alcohol humectant. Suitable polyhydric alcohols for use herein include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), trimethylol propane, neopentyl glycol, glycerine, ethoxylated glycerine and propoxylated glycerine. Preferred polyhydric alcohols of the present invention are polyhydric alcohols with 3 to 9 carbon atoms in the molecule. Suitable polyhydric alcohols include glycerine, butylene glycol, propylene glycol, dipropylene glycol, polyethylene glycol and derivatives thereof, hexane triol, ethoxylated glycerine and propoxylated glycerine, or mixtures thereof. More preferred for use in the present invention is glycerine. Preferably, the compositions of the present invention comprise from 5% to 30% humectant, more preferably from 7% to 25%.

It has been found that polyhydric alcohol humectants are desirable to counteract the drying effect that self-tanning agents have when topically applied, and also to chronically hydrate the skin in order to improve its skin barrier function. It has also been surprisingly found that polyhydric alcohol humectant increases the coloration of skin by the self tanning agent claimed (e.g. DHA), even when present at level lower than 20%. The improved coloration effect can be shown by measuring the skin coloration (e.g. on the forearm) obtained with a product according to the invention versus the same product without a polyhydric alcohol humectant. Skin coloration measurements can be made according to conventional means, for example using a Minolta™ Chromameter CR-300.

This increased coloration effect was particularly noticeable at levels of polyhydric alcohol humectant from 5 to 15% by weight, preferably from 8 to 13% and for self-tanning agent levels below levels used in conventional marketed self tanning products, i.e. levels at or below 5%, preferably at or below 4%, more preferably at or below 3%. Using lower levels of skin tanning agent also benefits the skin as these tend to damage skin over repeated uses. Whilst not wishing to be bound by theory, Applicant believes that the polyhydric alcohol humectant (e.g. glycerine) increase the water content of the skin horny layer, which in turn favours the self tanning process. It is also believed that polyhydric alcohol humectants may improve the skin condition, minimising any areas of dry or compromised skin. This is desirable as dry skin areas have uneven uptake of colour resulting in a blotchy or patchy result.

The compositions of the present invention further have a pH of from 3.5 to 4.5, preferably from 3.7 to 4.2. It has surprisingly been found that the polymers as defined in the present invention are stable at these low pHs, and in the presence of self-tanning agents. It has also surprisingly been found that by combining the polymers of the present invention with self-tanning agents at low pHs, stable emulsions can be formed that deliver relatively high proportions of active self-tanning agent to the skin following topical application, without the discoloration of the composition often associated with compositions comprising self-tanning agents. Without wishing to be bound by theory, it is believed that the combination of the polymers herein, and the low pH of the composition prevent the formation of methyl glyoxal, a degradation product of DHA. It has been suggested in U.S. Pat. No. 6,231,837 B1 that methyl glyoxal is responsible for the development of discoloration in formulations comprising DHA, and is also responsible for the production of an undesirable orange pigmentation when DHA is applied to the skin and is not present in a stabilised form. This may be the reason why the compositions of the present invention deliver self-tanning agents to the skin in a form that provides a natural tanning appearance, without the associated orange discoloration often associated with compositions containing self-tanning agents.

The compositions of the present invention may additionally comprise other humectants, including sodium 2-pyrrolidone-5-carboxylate (NaPCA); guanidine; glycolic acid and glycolate salts (e.g. ammonium and quaternary alkyl ammonium); aloe vera in any of its variety of, forms (e.g., aloe vera gel); hyaluronic acid, precursors and derivatives thereof (e.g., glucosamine and salt derivatives such as sodium hyaluronate); lactamide monoethanolamine; acetamide monoethanolamine; urea; and mixtures thereof.

The compositions of the present invention may further comprise from 0.1% to 15% of a skin care active that is stable in self-tanning systems. Preferably, the compositions of the present invention comprise from 0.25% to 5% of a skin care active. Stable skin care actives useful herein include betaine and its derivatives, tocopherol esters, skin lipids, or mixtures thereof. Incorporation of skin care actives in the present compositions enhances the skin benefit properties by providing reduced water loss and/or providing a desquamatory, keratolytic and rejuvenating effect when topically applied.

One class of skin care actives suitable for use herein are the betaines. Betaines suitable for use herein include those with a molecular weight of from greater than 75 to less than 260, preferably from greater than 75 to less than 200 and more preferably from greater than 75 to less than 180.

Betaines useful in the present invention comprise quaternary ammonium salts represented by the general formula (II) below:

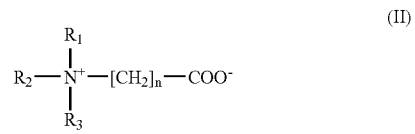

wherein $R_1$, $R_2$, and $R_3$ are independently selected from —H, —CH$_3$, —CH$_2$CH$_3$, and [—CH$_2$CH(OH)R$_4$, wherein R$_4$ is selected from —H, and C1 to C4 alkanes]; and wherein n=an integer from 1 to 3, preferably 1. Preferably $R_1$, $R_2$, and $R_3$ are all —$CH_3$, and n is 1; or $R_1$, $R_2$, and $R_3$ are all —$CH_3$, and n is 2; or $R_1$ and $R_2$ are —$CH_3$, $R_3$ is —H, and n is 1; or $R_1$ is —$CH_3$, $R_2$ and $R_3$ are —H, and n is 1; or $R_1$ and $R_2$ are [—$CH_2CH(OH)R_4$, $R_4$ is —H or —$CH_3$], $R_3$ is —H, and n is 1.

Further examples of betaines and derivatives thereof suitable for use in the present invention include betaines conforming to formula (II), wherein any two of $R_1$, $R_2$, and $R_3$ are independently selected from —H, and —$CH_3$, and the third moiety of $R_1$, $R_2$, and $R_3$ is selected from —($CH_2$)$mCH_3$ wherein m is 4 or 5; and wherein n=an integer from 1 to 3, preferably 1; preferably wherein $R_1$ and $R_2$ are —$CH_3$, $R_3$ is —($CH_2$)$mCH_3$ wherein m is 4, and n is 1.

Another class of betaine derivatives suitable for use in the present invention include cholines conforming to the general formula (III):

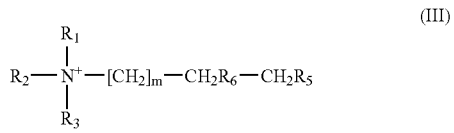

(III)

wherein $R_1$, $R_2$, $R_3$ $R_4$ are defined as in part (i) above; and wherein m is an integer from 0 to 2, and $R_5$ is selected from $PO_4$, $SO_4$ and $SO_3$, and $R_6$ is selected from H or OH. Preferred are cholines wherein $R_1$, $R_2$, and $R_3$ are —$CH_3$; m is 0; $R_6$ is H and $R_5$ is $PO_4$; or taurines wherein $R_1$, $R_2$, and $R_3$ are —$CH_3$; m is 0; and $R_5$ is $SO_3$, $R_6$ is H, or $R_1$, $R_2$, and $R_3$ are —$CH_3$; m is 1; $R_6$ is OH and $R_5$ is $SO_3$.

Further betaine derivatives suitable for use in the present invention are those comprising proline, carnitine, trimethylamineoxide, tricine, dimethyl proline and mixtures thereof.

Preferred for use herein are betaine or derivatives thereof comprising trimethylglycine, dimethyl glycine, sarcosine, trimethyl alanine, tricine, dimethyl proline, bicine, gamma-butyro betaine, trimethylamineoxide, proline, carnitine, and mixtures thereof, more preferably comprising trimethylglycine, tricine and dimethyl glycine; and mixtures thereof.

Non-limiting examples of preferred betaines or derivatives for use herein are identified immediately above. Non-limiting examples of preferred betaines or derivatives include trimethylglycine hydrate, available as TEGOCARE AP (RTM), from T. H. Goldschmidt (Germany), proline, available as proline, from Huls-Degussa (Germany), bicine, available as bicine, from Sigma Chemical (USA), and dimethylglycine, available as dimethylglycine from Sigma Chemical (USA).

Another class of skin care actives suitable for use herein includes the tocopherol esters, materials formed as a result of the condensation reaction between tocopherol and carboxylic acids. As used herein, "tocopherol esters" includes those materials conforming to the general formula (IV):

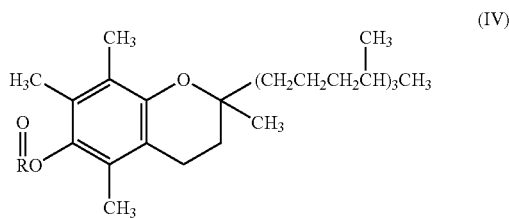

(IV)

wherein, R=OO is selected from linear, branched and cyclic carboxylic acids, preferably acetic acid, linoleic acid, nicotinic acid, oleic acid, or mixtures thereof. More preferably, the skin care active comprises tocopherol acetate, tocopherol nicotinate, or mixtures thereof. Non-limiting examples of commercially available tocopherol esters include tocopherol nicotinate from Ennagram UK Ltd, London, UK A further class of skin care actives suitable for use in the present invention are the skin lipids. Skin lipids perform an integral function of maintaining the water holding ability of the stratum corneum, regulating skin health. Non-limiting examples of skin lipids suitable for use herein include ceramides, cholesterols, fatty acids, or mixtures thereof. Ceramides, the primary component of skin lipids, and are comprised of sphingolipids consisting of a long chain amino alcohol (sphingosine or one of it's derivatives) to which a long chain fatty acid is linked via an amide bond. Natural or synthetic sources can be used, as can pseudo-ceramides. Preferably, the skin care active herein comprises ceramide, cholesterol, sphingosine, or mixtures thereof. Non-limiting examples of commercially available blends of skin lipids suitable for use herein include SK Influx from Cosmoferm.

The compositions of the present invention may further comprise a natural gum thickener. It has been found that the rheology and stability of the present compositions can be suitably modified and improved by the addition of low levels of natural gum thickeners, without the compositions becoming too stringy, or tacky. Natural gum thickeners suitable for use herein include xanthan gum, guar gum or its derivatives, chitosan, alginates, carragenan, locust bean gum, sclerotium, pectin, starches or their derivatives, or mixtures thereof, preferably xanthan gum. Where present, the natural gum thickeners are preferably present at levels of from 0.05% to 3%, more preferably from 0.05% to 1%, more preferably still from 0.05% to 0.5%.

The compositions of the invention are preferably formulated so as to have a product viscosity of at least 4,000 mPa·s and preferably in the range from 4,000 to 300,000 mPa·s, more preferably from 8,000 to 250,000 mPa·s and especially from 10,000 to 200,000 mPa·s and even more especially from 20,000 to 100,000 mPa·s (25° C., neat, Brookfield RVT, T-C Spindle at 5 rpms and Heliopath Stand). The compositions of the present invention may be formulated as an emulsion.

The cosmetic compositions herein are preferably in the form of a water-in-oil or oil-in-water emulsion. More preferably the cosmetic compositions herein are oil-in-water emulsions wherein the composition comprises one or more oil phases in an aqueous continuous phase, each oil phase comprising a single oily component or a mixture of oily components in miscible or homogeneous form. Different oil phases contain different materials, or different combinations of materials, from each other. The total level of oil phase components in the compositions of the invention is typically from 0.1% to 60%, preferably from 1% to 30%, more preferably from 3% to 20% and most preferably from 5% to 15%.

In preferred embodiments, the oil phase preferably comprises oily components such as a natural or synthetic oils selected from mineral, vegetable, and animal oils, fats and waxes, fatty acid esters, fatty alcohols, fatty acids and mixtures thereof. Preferred for use herein are for example, saturated and unsaturated fatty alcohols such as behenyl alcohol, cetyl alcohol and stearyl alcohol and hydrocarbons such as mineral oils or petrolatum.

The present compositions may further comprise a silicone phase. The silicone phase can comprise one or more silicone components such as silicone fluids, gums, and mixtures thereof. The, or each, silicone phase generally comprises from 0.1% to 20%, preferably from 0.2% to 10%, more preferably from 0.3% to 5%, of the composition.

Silicone components can be fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. The silicone fluids can be volatile or non-volatile.

The silicone components can also comprise silicone gums. The term "silicone gum" herein includes high molecular weight silicones having a weight average molecular weight in excess of about 200,000 and preferably from about 200,000 to about 4,000,000. Included are non-volatile polyalkyl and polyaryl siloxane gums. In preferred embodiments, a silicone oil phase comprises a silicone gum or a mixture of silicones including the silicone gum.

Useful herein are silicone/gum fluid blends. Preferred silicone-gum fluid blend based component for use in the compositions herein is a dimethiconol gum having a molecular weight of from 200,000 to 4,000,000 along with a silicone fluid carrier with a viscosity of 0.65 to 100 $mm^2 \cdot s^{-1}$. An example of this silicone component is Dow Corning Q2-1503 (85% 5 $mm^2 \cdot s^{-1}$ Dimethicone Fluid/15% Dimethiconol) and Dow Corning Q2-1501 available from Dow Corning.

The topical compositions of the present invention preferably comprise emollient materials including branched chain hydrocarbons having an weight average molecular weight of from 100 to 15,000, preferably from 100 to 1000; compounds of formula V:

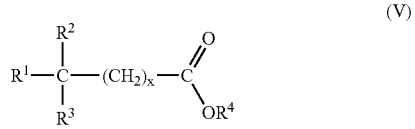

(V)

wherein $R^1$ is selected from H or $CH_3$, $R^2$, $R^3$ and $R^4$ are independently selected from $C_1$-$C_{20}$ straight chain or branched chain alkyl, and x is an integer of from 1-20; and compounds having the formula VI:

(VI)

wherein $R^5$ is selected from optionally hydroxy or $C_1$-$C_4$ alkyl substituted benzyl and $R_6$ is selected from $C_1$-$C_{20}$ branched or straight chain alkyl; and mixtures thereof.

Suitable branched chain hydrocarbons for use herein include isododecane, isohexadecane, isoeicosane, isooctahexacontane, isohexapentacontahectane, isopentacontaoctactane, and mixture thereof. Suitable ester emollient materials of Formula (VI) include but are not limited to C12-15 alkyl benzoates.

Preferred emollients for use herein are isohexadecane, isononyl isononanoate, methyl isostearate, isopropyl isostearate, and mixtures thereof. A further emollient suitable for use in the composition of the present invention is petrolatum.

The emollient material is preferably present in the compositions at a level of from about 0.1% to about 10%.

The present compositions herein may comprise an emulsifier and/or surfactant, generally to help disperse and suspend the discontinuous phase within the continuous phase. For convenience hereinafter emulsifiers will be referred to under the term 'surfactants', thus 'surfactant(s)' will be used to refer to surface active agents whether used as emulsifiers or for other surfactant purposes such as skin cleansing. Known or conventional surfactants can be used in the composition, provided that the selected agent is chemically and physically compatible with essential components of the composition, and provides the desired characteristics.

The compositions of the present invention preferably comprise from 0.05% to 15% of a surfactant or mixture of surfactants. The exact surfactant or surfactant mixture chosen will depend upon the pH of the composition and the other components present. Surfactants suitable for use herein include non-ionic, cationic, anionic, zwitterionic, amphoteric surfactants, or mixtures thereof.

Preferred surfactants are nonionic. Among the nonionic surfactants that are useful herein are those that can be broadly defined as condensation products of long chain alcohols, e.g. $C_{8-30}$ alcohols, with sugar or starch polymers, i.e., glycosides. Preferred examples include a mixture of cetearyl glucosides and cetearyl alcohols such as those commercially available as Montanov 68™ from Seppic and Emulgade PL68/50™ available from Henkel.

Other useful nonionic surfactants include the condensation products of alkylene oxides with fatty acids (i.e. alkylene oxide esters or diesters of fatty acids). Other nonionic surfactants are the condensation products of alkylene oxides with fatty alcohols (i.e. alkylene oxide ethers of fatty alcohols). Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Still other useful nonionic surfactants include polyhydroxy fatty acid amide surfactants, which are described in more detail in WO98/04241.

Another emulsifier useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20}$. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate. This is commercially available from ICI under the name Arlatone 2121™.

Preferred among the nonionic surfactants are those selected from the group consisting of cetearyl glucosides, cetearyl alcohols, PEG-100 stearate, sorbitan stearate and mixtures thereof.

Emulsions of the present invention may include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. Other examples include alkyl-modified dimethicone copolyols, i.e., compounds that contain $C_2$-$C_{30}$ pendant side chains. Still other useful dimethicone copolyols include materials having various cationic, anionic, amphoteric, and zwitterionic pendant moieties.

The composition of the present invention comprises water. Preferably, water comprises from 30% to 85% by weight of the composition, more preferably 50% to 75% by weight of the composition.

The compositions of the present invention can further comprise optional ingredients. Optional ingredients are well known in the art, and can be added without reacting with and altering the chemistry therein. Optional ingredients include additional actives, neutralizing agents, sunscreening agents and mixtures thereof.

The cosmetic compositions of the present invention can be formulated in a form suitable for topical application. Non-limiting examples of such forms include self-tanning compositions, topical compositions, sprays, aerosol sprays, spray gels, lotions, creams and mousses. Preferably, the cosmetic compositions of the present invention are in the form of a self-tanning composition or a lotion.

Alternatively, the cosmetic compositions of the present invention may be used in combination with a substrate to form a skin care kit. The skin care kits of the present invention comprise the cosmetic compositions herein, and a substrate. Non-limiting examples of substrates useful herein include wet wipes, towlettes, foam sponges, roller ball delivery systems and the like. When used in this form, the substrate may be impregnated, coated, or soaked with the compositions herein. Alternatively, the compositions herein may be applied to the substrate by the consumer immediately prior to application to the skin. The skin care kits herein are desirable to prevent the accidental application of the cosmetic composition to areas of the body where it is not required or desired.

The compositions of the present invention are useful for regulating skin condition and enhancing skin tone. Such regulation of skin condition can include cosmetic prophylactic and therapeutic regulation. It may also include providing a more noticeable improvement, both tactile and visual, in the appearance and feel of the skin of a mammal. For example, such regulating methods are directed to making the skin feel softer, reducing the appearance of fine lines and wrinkles, and improving skin health. Also, such methods provide an enhancement of skin tone. The compositions of the present invention enhance skin tone by imparting a natural-looking tan to the skin of a consumer following topical application, without the appearance of an orange colour. This is believed to be due to the improved stabilisation of the self-tanning agent in the compositions, and increased delivery of the self-tanning agent in its active form.

Regulating skin condition involves topically applying to the skin a safe and effective amount of a composition of the present invention. In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are, in mg composition/$cm^2$ skin, from 0.1 mg/$cm^2$ to 30 mg/$cm^2$. A particularly useful application amount is 0.5 mg/$cm^2$ to 20 mg/$cm^2$.

Regulating skin condition is preferably practiced by applying a composition which is intended to be left on the skin for some aesthetic, cosmetic, prophylactic, therapeutic or other benefit (i.e., a "leave-on" composition). After applying the composition to the skin, it is preferably left on the skin for a period of at least 15 minutes, more preferably at least 30 minutes, even more preferably at least 1 hour, still more preferably for at least several hours, e.g., up to 12 hours.

Another approach to ensure a continuous exposure of the skin to at least a minimum level of the skin care active is to apply the compound by use of a patch applied, e.g., to the face. The patch can be occlusive, semi-occlusive or non-occlusive and can be adhesive or non-adhesive. The composition can be contained within the patch or be applied to the skin prior to application of the patch. The patch can also include additional actives such as chemical initiators for exothermic reactions such as those described in U.S. Pat. Nos. 5,821,250, 5,981,547, and 5,972,957. The patch is preferably left on the skin for a period of at least 5 minutes, more preferably at least 15 minutes, more preferably still at least 30 minutes, even more preferably at least 1 hour, still more preferably at night as a form of night therapy.

The compositions of the present invention may be manufactured according to a certain method. The method for manufacturing the compositions herein comprises the steps of forming a premix comprising the branched and/or cross-linked anionic polyelectrolyte polymer at a temperature of from 50° C. to 70° C. Subsequently, said premix is cooled to a temperature of less than 40° C. and the self-tanning agent is added. It is desirable to form the compositions of the present invention in this way to maintain the stability of the self-tanning agent during manufacture and subsequent storage. Without wishing to be bound by theory, it is believed that adding the self-tanning agent to a premix already comprising the branched and/or cross-linked anionic polyelectrolyte polymer at a temperature of less than 40° C. inhibits the potential for the self-tanning agent to react with the polymer and other ingredients therein, thereby enhancing the amount of active self-tanning agent present in the composition.

EXAMPLES I-V

| INGREDIENTS | Example 1 (w/w %) | Example 2 (w/w %) | Example 3 (w/w %) | Example 4 (w/w %) | Example 5 (w/w %) |
|---|---|---|---|---|---|
| DEIONISED WATER | QS | QS | QS | QS | QS |
| GLYCERINE | 7.0 | 10.0 | 10.0 | 10.0 | 15.0 |

-continued

| INGREDIENTS | Example 1 (w/w %) | Example 2 (w/w %) | Example 3 (w/w %) | Example 4 (w/w %) | Example 5 (w/w %) |
| --- | --- | --- | --- | --- | --- |
| SK INFLUX[1] | — | — | — | 1.0 | 1.0 |
| TOCOPHEROL NICOTLNATE[2] | — | 3.0 | — | — | — |
| VITAMIN E ACETATE | 0.25 | — | 0.5 | — | 0.25 |
| ISOHEXADECANE | 3.0 | 3.0 | 3.0 | 3.0 | 3.0 |
| ISOPROPYL ISOSTEARATE | 1.50 | 1.50 | 1.50 | 1.50 | 1.50 |
| COCONUT OIL FRACTIONATED | 0.2 | 0.2 | 0.2 | 0.2 | 0.2 |
| PETROLATUM | 2.0 | 2.0 | 2.0 | 2.0 | 2.0 |
| SIMUGEL NS[3] | 1.0 | 1.5 | 1.5 | 1.5 | 2.0 |
| XANTHAN GUM | 0.1 | 0.1 | 0.1 | 0.2 | 0.2 |
| STEARYL ALCOHOL | 0.6 | 0.6 | 0.6 | 0.6 | 0.6 |
| CETYL ALCOHOL | 0.5 | 0.5 | 0.5 | 0.5 | 0.5 |
| BEHENYL ALCOHOL | — | 0.4 | 0.4 | 0.4 | 0.4 |
| PEG-100 STEARATE | 0.1 | 0.1 | 0.1 | 0.1 | 0.1 |
| EMULGADE[4] | 0.2 | 0.2 | 0.2 | 0.2 | 0.2 |
| NYLONPOLY WL10[5] | — | 1.0 | — | 1.0 | 1.0 |
| DRY FLO PLUS[6] | 0.5 | 1.0 | 0.5 | 1.0 | 1.0 |
| MICROTHENE[7] | 0.5 | — | 0.5 | — | — |
| DHA[8] | 1.0 | 1.5 | 2.5 | 1.5 | 5.0 |
| ERYTHRULOSE[9] | — | — | — | 0.5 | — |
| ETHYL PARABEN | 0.15 | 0.15 | 0.15 | 0.15 | 0.15 |
| PROPYL PARABEN | 0.07 | 0.07 | 0.07 | 0.07 | 0.07 |
| DISODIUM EDTA | 0.1 | 0.1 | 0.1 | 0.1 | 0.1 |
| BENZYL ALCOHOL | 0.25 | 0.25 | 0.25 | 0.25 | 0.25 |
| DC 1503 | 1.0 | 1.0 | 1.0 | 1.0 | 1.0 |
| PERFUME | 0.2 | 0.2 | 0.2 | 0.2 | 0.2 |

[1]SK Influx: Supplied by Goldschmidt AG, Goldschmidtstrasse 100, D-45127 Essen, Germany.
[2]Tocopherol Nicotinate: Supplied by Ennagram UK Ltd, Edelman House, 1238 High Road, Whetstone, London.
[3]Simugel NS: Supplied by Seppic, 75 Quai D'Orsay, Paris
[4]Emulgade: Supplied by Cognis Deutschland GmbH, Paul-Thomas Strasse 56, D-40551 Dusseldorf, Germany.
[5]Nylonpoly WL10: Supplier Optima Chemicals, Unit 17, Chiltern Business Village, Arundel Road, Uxbridge, Middlesex, UB8 2SN
[6]Dry Flo: Supplied by National Starch Chemical Company, 10, Finderne Avenue, Bridgewater, NJ 08807, USA
[7]Microthene: Supplied by Equistar Chemicals, 1221 McKinney Street, Suite 700, Houston, TX 77252–2583
[8]DHA: Supplied by Merck GmBH, Frankfurter Strasse 250, 64293 Darmstadt, Germany.
[9]Erythrulose: Supplied by Pentapharm, Engelgasse 109, 4002 Basel, Switzerland.

The compositions are made as follows:

A water phase is prepared by admixing all water soluble ingredients (including xanthan gum), except DHA and Erythrulose, in water and heating to 80° C. A second premix is prepared by admixing of the oil soluble ingredients except the silicone oil (DC 1503) and heating also to 80° C. The oil phase is added to the water phase and sheared to form an emulsion.

The emulsion is cooled to 60° C. and the polymeric thickener (Simugel NS) is then added. At 45-50° C. the benzyl alcohol and DC1503, and particles are added and the resulting product is sheared to ensure particle dispersion, de-agglomeration and homogeneity. The composition can then be cooled to below 40° C. and DHA, Erythrulose and perfume can be added. The product can then be prepared for packaging.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition comprising:
   a) a self-tanning agent conforming to the general formula;

$$R_2 \overset{O}{\underset{}{\diagup\kern-0.7em\diagdown}} \underset{OH}{\overset{}{\diagup\kern-0.7em\diagdown}} R_1$$

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$; and a) a branched and/or cross-linked anionic polyelectrolyte polymer, said anionic polyelectrolyte polymer comprising;
  i) from about 58.7% to about 89.9999% by weight of the polyelectrolyte polymer of a monomer comprising a strongly acidic function;
  ii) from about 9.9999% to about 40% by weight of the polyelectrolyte polymer of at least one hydroxy alkyl acrylate neutral monomer; and
  iii) from about 0.0002% to about 1.3% by weight of the polyelectrolyte polymer of a diethylenic or polyethylenic cross-linking agent;
b) a polyhydric alcohol humectant;
said composition further having a pH of from about 3.5 to about 4.5.

2. The cosmetic composition according to claim 1 wherein the strongly acidic function of said monomer of part i) comprises partially and totally salified sulphonic acid function, partially and totally salified phosphonic acid function and mixtures thereof.

3. The cosmetic composition according to claim 1 wherein the neutral monomer comprises 2-hydroxyethylacrylate, 2,3-dihydroxypropyl acrylate, 2-hydroxy-ethyl methacrylate and 2,3-dihydroxypropyl methacrylate, or an ethoxylated derivative having a molecular weight of from 400 to 1000 and mixtures thereof.

4. The cosmetic composition according to claim 3 wherein the neutral monomer comprises 2-hydroxy ethyl acrylate.

5. The cosmetic composition according to claim 1 wherein the cross-linking and branching agents comprise ethylene glycol dimethacrylate, sodium diallyloxyacetate, ethylene glycol diacrylate, diallylurea, trimethylolpropane triacrylate, methylene bisacrylamide and mixtures thereof.

6. The cosmetic composition according to claim 5 wherein the cross-linking and branching agents comprise methylene bisacrylamide.

7. The cosmetic composition according to claim 1 wherein the branched and cross-linked anionic polyelectrolyte polymers comprise:
  i) from about 58.7% to about 89.9999% by weight of the polyelectrolyte polymer of the partially and/or totally salified alkali metal salt or ammonium salt of 2-methyl-2-[(1-oxo-2-propenyl)-1-propanesulphonic acid;
  ii) from about 9.9999% to about 40% by weight of the polyelectrolyte polymer of 2-hydroxyethylacrylate; and
  iii) from about 0.0002% to about 1.3% by weight of the polyelectrolyte polymer of methylene bisacrylamide.

8. The cosmetic composition according to claim 1 comprising from about 0.1% to about 2% of branched and cross-linked anionic polyelectrolyte polymers.

9. The cosmetic composition according to claim 1 comprising from about 0.1% to about 10% of the self-tanning agent.

10. The cosmetic composition according to claim 1 wherein the self-tanning agent comprises dihydroxyacetone, erythrulose and mixtures thereof.

11. The cosmetic composition according to claim 1 wherein the pH of the composition is from about 3.7 to about 4.2.

12. The cosmetic composition according to claim 1 comprising from about 5% to about 30% by weight of the composition of a polyhydric alcohol humectant.

13. The cosmetic composition according to claim 12 comprising from about 5% to about 15% by weight of the composition of a polyhydric alcohol humectant.

14. The cosmetic composition according to claim 1 wherein said polyhydric alcohol humectant is selected from the group consisting of propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol, hexane triol, trimethylol propane, neopentyl glycol, glycerine, ethoxylated glycerine and propoxylated glycerine, and mixtures thereof.

15. The cosmetic composition according to claim 14 wherein said polyhydric alcohol humectant comprises glycerine.

16. The cosmetic composition according to claim 1 further comprising a skin care active.

17. The cosmetic composition according to claim 16, wherein said skin care active comprises betaine and its derivatives, tocopherol esters, skin lipids and mixtures thereof.

18. The cosmetic composition according to claim 17, wherein said skin care active comprises trimethyl glycine, tocopherol nicotinate, tocopherol acetate, ceramide, cholesterol, sphingosineand mixtures thereof.

19. The cosmetic composition according to claim 16 comprising from about 0.1% to about 15% of said skin care active.

20. The cosmetic composition according to claim 1 further comprising a natural gum thickener.

21. The cosmetic composition according to claim 20 comprising from about 0.05% to about 3% by weight of the composition of a natural gum thickener.

22. The cosmetic composition according to claim 20 wherein said natural gum thickener comprises xanthan gum, guar gum or its derivatives, chitosan, alginates, carageenan, locust bean gum, sclerotium, pectin, starches or their derivativesand mixtures thereof.

23. The cosmetic composition according to claim 22 wherein said natural gum thickener comprises xanthan gum.

24. The cosmetic composition according to claim 1, wherein the cosmetic composition is in the form of an emulsion.

25. The cosmetic composition according to claim 24 wherein the cosmetic composition is in the form of an oil-in-water emulsion.

26. The cosmetic composition according to claim 25 wherein the oil phase comprises from about 0.1% to about 60% by weight of the composition.

27. A method of manufacturing the composition according to claim 1 comprising the steps of forming a premix comprising said branched and/or cross-linked anionic polyelectrolyte polymer at a temperature of from about 50° C. to about 70° C., cooling said premix to a temperature of less than about 40° C. and adding said self-tanning agent.

* * * * *